United States Patent
Liang et al.

(10) Patent No.: US 10,287,240 B2
(45) Date of Patent: May 14, 2019

(54) METHOD FOR RESOLUTION OF CITALOPRAM INTERMEDIATE 5-CYANO DIOL

(71) Applicant: ZHEJIANG HUAHAI PHARMACEUTICALS CO., LTD., Zhejiang (CN)

(72) Inventors: Zunjun Liang, Zhejiang (CN); Siqi Hu, Zhejiang (CN); Caihua Peng, Zhejiang (CN); Wenfeng Huang, Zhejiang (CN); Qifeng Lu, Zhejiang (CN); Guoliang Tu, Zhejiang (CN)

(73) Assignee: Zhejiang Hushai Pharmaceuticals Co., Ltd., Zhejiang (CN)

( * ) Notice: Subject to any disclaimer, the term of this patent is extended or adjusted under 35 U.S.C. 154(b) by 0 days.

(21) Appl. No.: 15/521,776

(22) PCT Filed: Nov. 14, 2014

(86) PCT No.: PCT/CN2014/091139
§ 371 (c)(1),
(2) Date: Apr. 25, 2017

(87) PCT Pub. No.: WO2016/074225
PCT Pub. Date: May 19, 2016

(65) Prior Publication Data
US 2017/0240505 A1    Aug. 24, 2017

(51) Int. Cl.
*C07C 253/34* (2006.01)
*C07C 255/59* (2006.01)
*C07C 69/78* (2006.01)

(52) U.S. Cl.
CPC ............ *C07C 253/34* (2013.01); *C07C 69/78* (2013.01); *C07C 255/59* (2013.01); *C07B 2200/13* (2013.01)

(58) Field of Classification Search
CPC .................................................. C07C 253/34
See application file for complete search history.

(56) References Cited

U.S. PATENT DOCUMENTS

2011/0092719 A1* 4/2011 Giridhar ............... C07C 255/59
549/467

FOREIGN PATENT DOCUMENTS

| CN | 101265215 A | 9/2008 |
|---|---|---|
| CN | 101386583 A | 3/2009 |
| CN | 102190600 A | 9/2011 |
| EP | 2061753 B1 | 8/2011 |
| WO | 2006106531 A1 | 10/2006 |
| WO | 2007012954 A1 | 2/2007 |
| WO | 2007082771 A1 | 7/2007 |
| WO | 2008059514 A2 | 5/2008 |
| WO | 2010004575 A2 | 1/2010 |

OTHER PUBLICATIONS

Sigma-Aldrich, Product Specification Sheet for Diethyl ether, retrieved Mar. 13, 2018, p. 1. (Year: 2018).*
International Search Report for PCT/CN2014/091139 dated Aug. 17, 2015.
Supplementary European Search Report for EP 14 90 5690 dated Apr. 19, 2018.

* cited by examiner

*Primary Examiner* — Rebecca L Anderson
*Assistant Examiner* — Karen Cheng
(74) *Attorney, Agent, or Firm* — Abelman, Frayne & Schwab

(57) ABSTRACT

Provided is a method for resolution of formula 4-[4-dimethylamino-1-(4-fluorophenyl)-1-hydroxylbutyl]-3-hydroxy-methyl benzonitrile as an enantiomer thereof, comprising the following steps: a salt of (S)-4-[4-dimethylamino-1-(4-fluorophenyl)-1-hydroxylbutyl]-3-hydroxymethyl benzonitrile with a resolving agent D-(+)di-p-toluoyl tartaric acid was crystallized in a resolving solvent; the method is characterized in that the resolving solvent is an ether solvent. Also provided is a new crystal form of the resolved intermediate.

5 Claims, 3 Drawing Sheets

METHOD FOR RESOLUTION OF CITALOPRAM INTERMEDIATE 5-CYANO DIOL

RELATED APPLICATIONS

This application is a national phase of International Application No. PCT/CN20141091139 filed Nov. 14, 2014, incorporated by reference in its entirety.

TECHNICAL HELD

The present invention relates to a method for resolution of citalopram intermediate 5-cyano diol.

TECHNICAL BACKGROUND

Citalopram is an important anti-depression drug, which is a selective 5-hydroxytryptamine (5-HT) reuptake inhibitor with S-configuration, and the isomer with S-citalopram has an anti-depression effect that is 100 times more than the isomer of the opposite configuration—R-citalopram, therefore, it has a much better curative effect and much less dosage. In the market of Europe and America, the S-isomer is mainly sold, and it is prepared by the cyclization and salt-forming reaction of S-5-cyano did (IV).

S-5-cyano diol (IV) is the key initial raw material for producing S-citalopram, in industrial production, generally, it is prepared by forming a salt from racemic 5-cyano diol (I) and a resolving agent D-(+)di-p-toluoyl tartaric acid (II) (abbr. DPTTA) in alcohols and mixed solvents comprising alcohols, separating the (S)-5-cyano did resolved intermediate (III) by crystallization, then subjecting to ionization by a free base. The resolution process can be represented as follows:

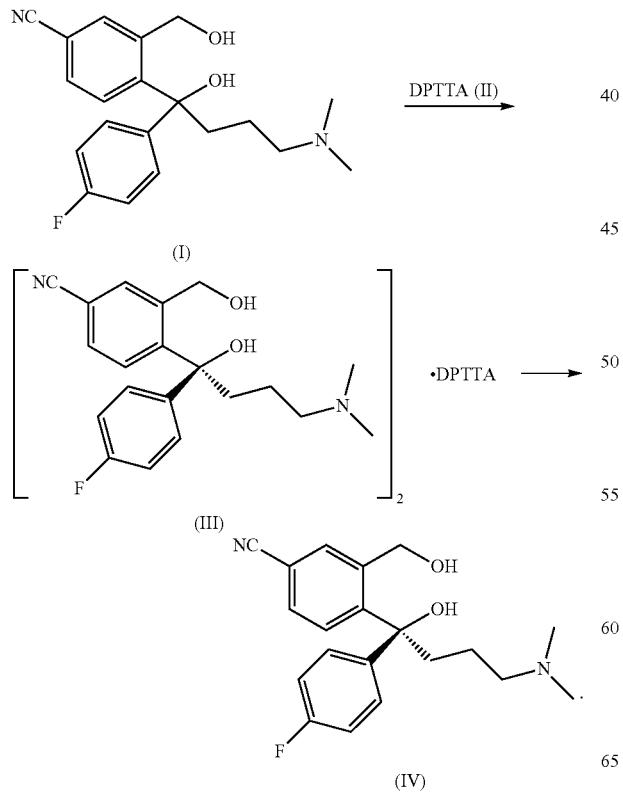

The structure of the resolving agent DPTTA is as follows:

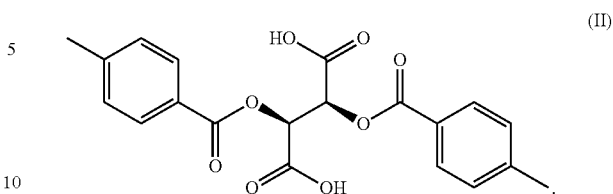

In U.S. Pat. No. 4,943,590 and WO2007/012954, it is described that the (S)-5-cyano diol resolved intermediate (III) is obtained by the resolution of racemic 4-(4-dimethylamino-1-p-fluorophenyl-1-hydroxybutyl)-3-(hydroxymethyl) benzonitrile by DPTT in isopropanol. The particle size of the crystals of the (a)-5-cyano diol resolved intermediate (III) obtained by the method are small and they are hard to be filtered, which does not meet the requirement of large-scale industrial production, and the chiral purity of the obtained crude (S)-5-cyano dial resolved intermediate (III) is low, the crude product needs to be repurified by isopropanol during the production to be qualified, thus the operation is very complex.

US2009/0069582 reports the preparation of the (S)-5-cyano diol resolved intermediate (III) with DPTT as the resolving agent, resolving racemic 5-cyano dial (I) from the solvent system comprising 1-propanol. The chiral purity of the method is generally low, two times of refinements are needed during production to obtain the (S)-5-cyano diol resolved intermediate (III) with qualified chiral purity, and the yield of the method is smaller than 38% at present.

SUMMARY OF THE INVENTION

According to one aspect of the present invention, a method of high efficiently resolving 5-cyano diol (I) is provided, comprising the following steps: a salt of (S)-4-[4-dimethylamino-1-(4-fluorophenyl)-1-hydroxylbutyl]-3-hydroxymethyl benzonitrile of formula IV with a resolving agent D-(+)di-p-toluoyl tartaric acid of formula II was crystallized in a resolving solvent; characterized in that the resolving solvent is an ether solvent.

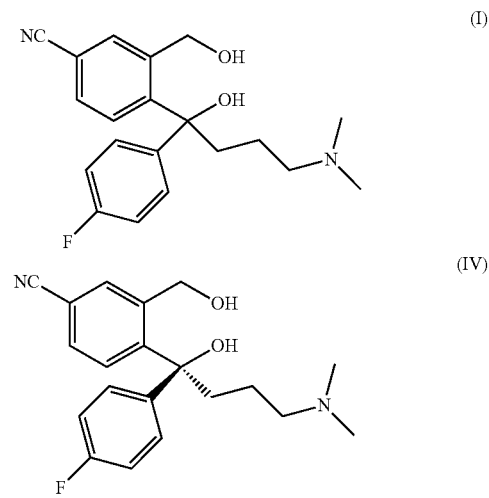

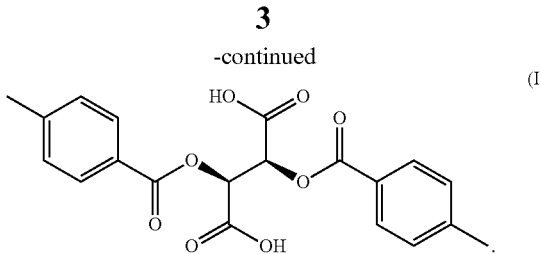

(II)

The ether solvent is selected from: tetrahydrofuran, methyltetrahydrofuran, cyclopentyl methyl ether, isopropyl ether, dioxane, ethylene glycol monomethyl ether, ethylene glycol dimethyl ether, ethylene glycol diethyl ether, ethylene glycol dibutyl ether, diethylene glycol dimethyl ether, propylene glycol dimethyl ether and propylene glycol diethyl ether. Preferably, the ether solvent contains a certain amount of water, the volume percentage of water in the solvent is 0.2%-10%, furthermore, the volume percentage of water is preferably 0.2%-5%. Under the condition that the solvent contains water, the crystal particles of the resolved intermediate are more structured and the particle sizes are bigger, thus they are easy to be filtered, which is convenient to operate during production. According to a second aspect of the present invention, it is found that when ether solvent without water is used, a new crystal form B of the resolved intermediate of formula (III) is obtained, the DSC thermogram of the crystal form obtained from differential scanning calorimetry (heating rate 10° C./minute) shows an endothermic peak onset 135.20° C., peak 150.35° C.

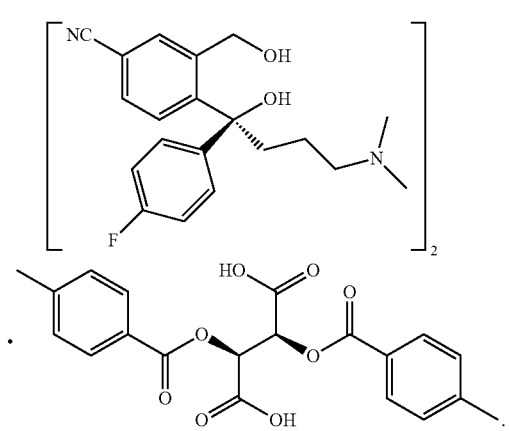

(III)

The DSC thermogram of form B is shown in FIG. 2.

According to a third aspect of the present invention, it is found that when ether solvent with a water volume percentage of 0.2%-10% is used as a resolving solvent, crystal form C of the resolved intermediate of formulat (III') is obtained,

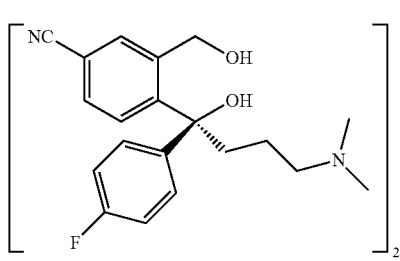

(III')

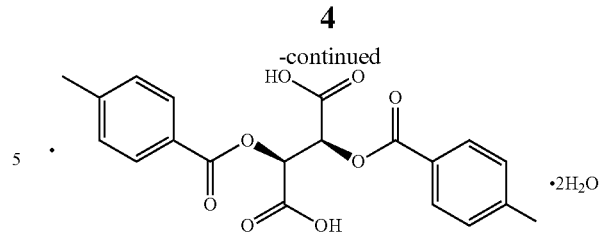

(II)
•2H$_2$O

The DSC thermogram of form C obtained by differential scanning calorimetry (heating rate 10° C./minute) shows two endothermic peaks, which are onset 107.40° C., peak 114.11° C., and onset 144.44° C., peak 154.55° C. respectively.

The DSC thermogram of form C is shown in FIG. 3.

The thermogravimetric analysis (TGA) thermogram of form C is shown in FIG. 4.

From the TGA thermogram of form C, it can be seen the data of losing one molecular of water (1.66%), the temperature of dehydration: 120-130° C., when another molecular of water is lost, it is 3.05% in the thermogram, the temperature of dehydration: 140-150° C., the temperature of dehydration overlaps with the endothermic decomposition peak after melting, the interference is relatively large, thus there's deviation for the data of weight loss. Karl Fischer method measure the water content of form C is 3.0%, which is close to two crystal water.

The powder X-ray diffraction (PXRD) pattern of form C is shown in FIG. 5, the data of the angle and the intensity of the diffraction peak are shown in table 1 below:

TABLE 1

| Diffraction angle (2θ, °) | Intensity (I/I$_0$, %) |
|---|---|
| 6.99791 | 100.00 |
| 7.2123 | 45.07 |
| 7.7337 | 3.65 |
| 9.5913 | 3.26 |
| 10.2215 | 2.07 |
| 11.1993 | 1.16 |
| 13.2329 | 1.37 |
| 14..0106 | 3.21 |
| 14.6793 | 1.62 |
| 15.4477 | 1.47 |
| 16.1794 | 5.38 |
| 17.3132 | 4.74 |
| 17.8285 | 5.88 |
| 18.3324 | 3.39 |
| 18.9355 | 4.97 |
| 20.3996 | 9.00 |
| 21.1254 | 8.22 |
| 21.7329 | 6.48 |
| 23.2205 | 2.61 |
| 24.0681 | 3.77 |
| 26.6347 | 2.17 |

The crystal structures of the (S)-5-cyano diol resolved intermediates form B and form C prepared according to the present invention are different from the (S)-5-cyano diol resolved intermediates obtained from existing methods.

The resolving methods of WO2007/012954 and US 2009/0069582 are repeated, the crystal forms of the (S)-5-cyano diol intermediate obtained are the same, it is named as form A in the present description. The DSC thermogram of form A obtained through differential scanning calorimetry (heating rate 19° C./minute) is shown in FIG. 1, which shows an endothermic peak, onset 131.20° C., peak 142.90° C. The advantages of the resolving method of the present invention are:

(1) The resolving effect is good, the yield is high and the chiral purity is high, which is generally greater than 99.0%, the operation of post-processing is simple, second refinement is not required and the efficient is high;

(2) A single solvent that contains water or does not contain water can be used, the recovery rate of the solvent is high, the cost of production is low;

(3) The crystallinity is good, the crystal particles are large, it is fast and easy to separate by centrifugation, and the efficient is high.

EMBODIMENTS

Example 1

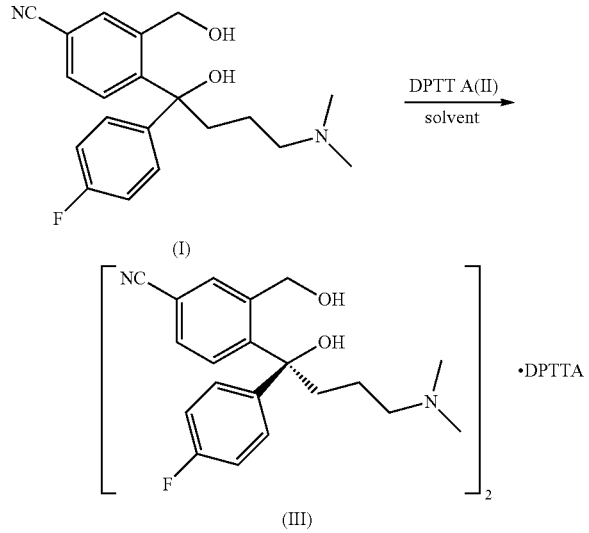

Figure 1:
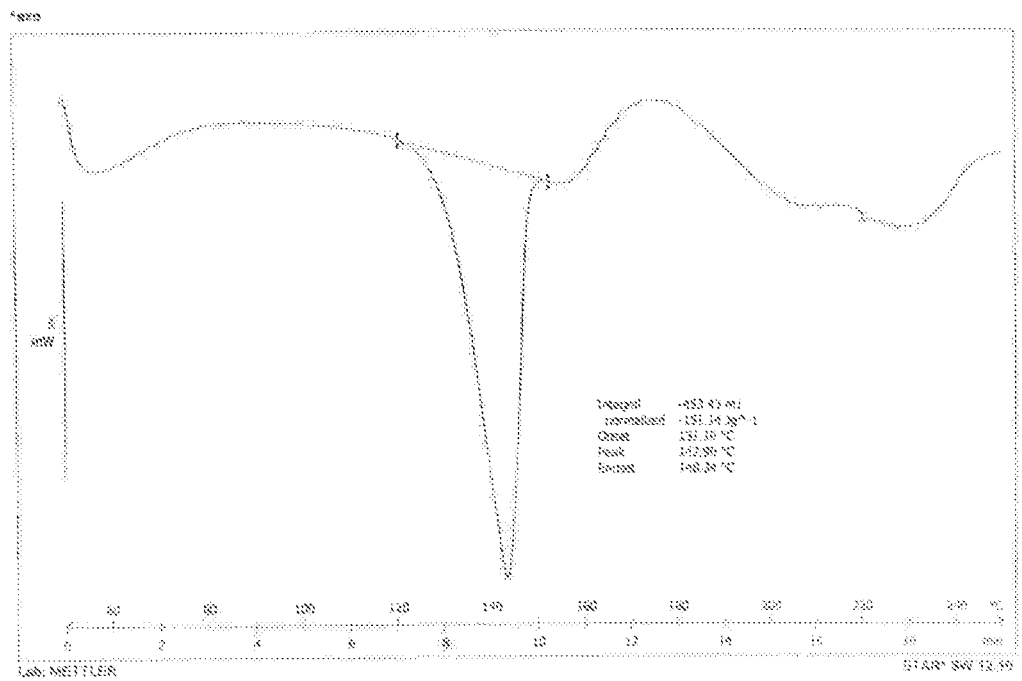
FIG. 1 is the DSC thermogram of form A of (S)-5-cyano diol resolved intermediate (III).
Figure 2:
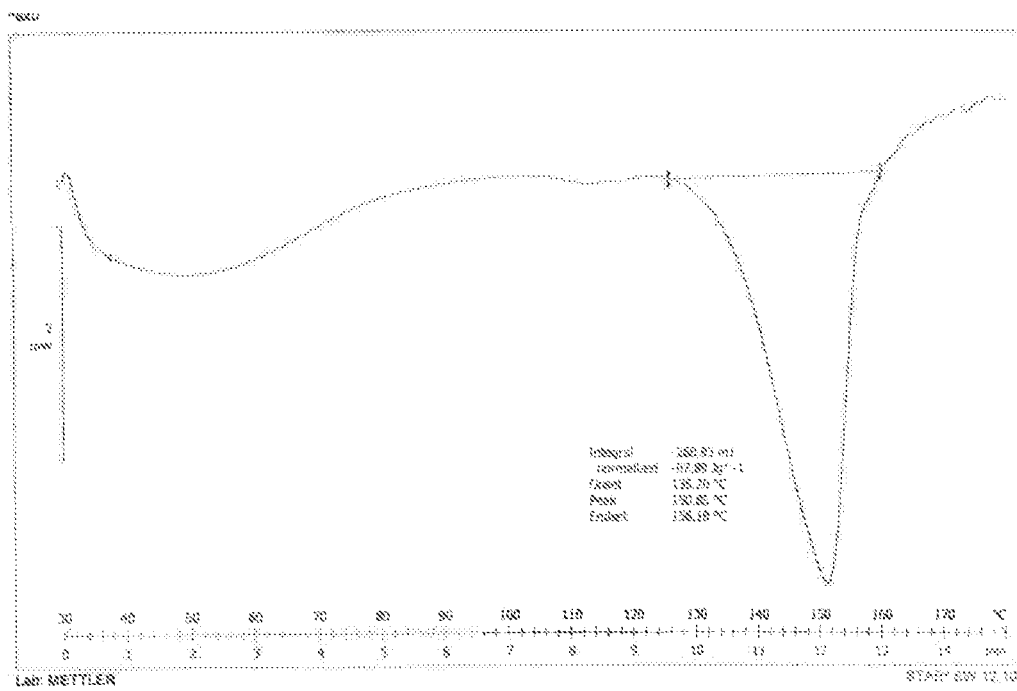
FIG. 2 is the DSC thermogram of form B of (S)-5-cyano diol resolved intermediate (III).
Figure 3:
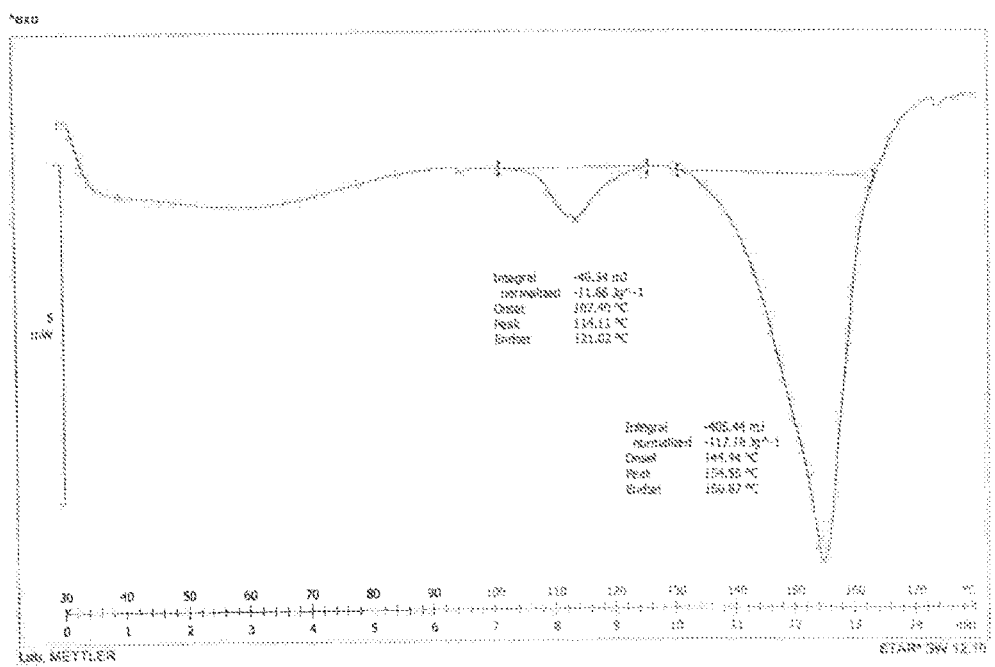
FIG. 3 is the DSC thermogram of form C of (S)-5-cyano diol resolved intermediate dihydrate (III').
Figure 4:
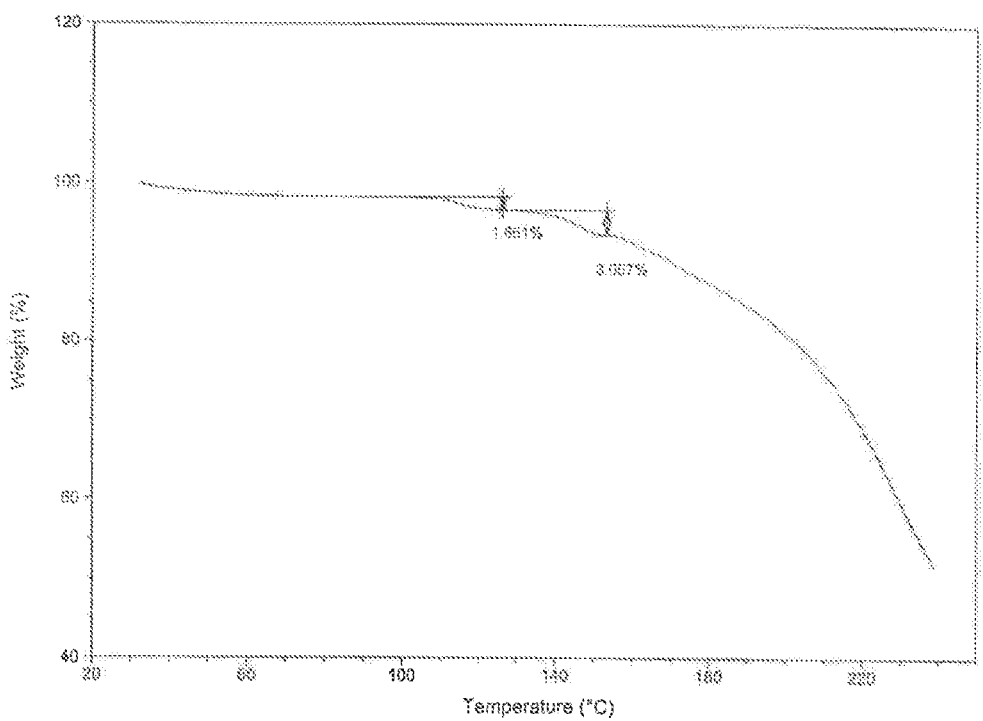
FIG. 4 is the TGA thermogram of form C of (S)-5-cyano diol resolved intermediate dihydrate (III').
Figure 5:
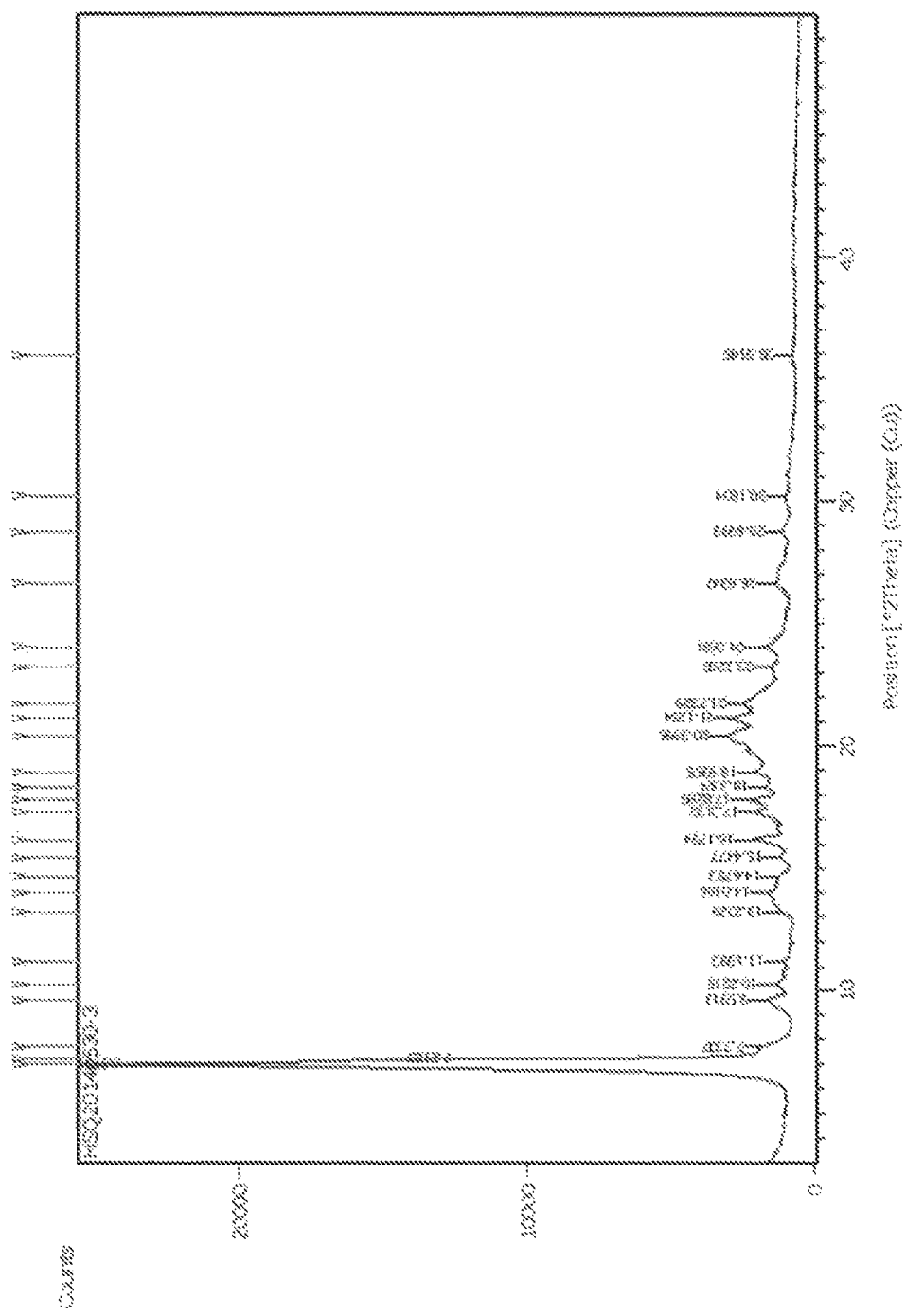
FIG. 5 is the PXRD pattern of form C of (S)-5-cyano diol resolved intermediate dihydrate (III').

Racemic 5-cyano diol (34.2 g, 1.0 equivalent), D-(+)di-p-toluoyl tartaric acid (20.1 g, 0.52 equivalent) were added, an ether solvent (513 mL) was added, the temperature was increased to 50~60° C., the reaction was stirred for 2 hours. The temperature was decreased slowly to 30° C., a large amount of solids were precipitated, stirred for 60 minutes with the temperature kept. Filtered, the filter cake was washed by 30 mL ether solvent once. The filter cake was vacuum dried at 50° C. to obtain the resolved intermediate (III).

The results with different ether solvents are shown in table 2:

TABLE 2

| Solvent | Yield | Chiral purity |
|---|---|---|
| Tetrahydrofuran | 48.5% | 99.8% |
| Methyltetrahydrofuran | 47.3% | 99.7% |
| Cyclopentyl methyl ether | 48.2% | 99.2% |
| Diethyl ether | 44.7% | 98.7% |
| Isopropyl ether | 45.5% | 99.1% |
| Dioxane | 45.1% | 99.5% |
| Diethylene glycol dimethyl ether | 46.0% | 99.3% |
| Ethylene glycol monomethyl ether | 42.5% | 98.4% |
| Ethylene glycol dimethyl ether | 45.7% | 99.2% |
| Ethylene glycol diethyl ether | 46.1% | 99.1% |
| Ethylene glycol dibutyl ether | 45.8% | 99.4% |
| Propylene glycol dimethyl ether | 45.1% | 99.0% |
| Propylene glycol diethyl ether | 46.2% | 99.2% |

Example 2

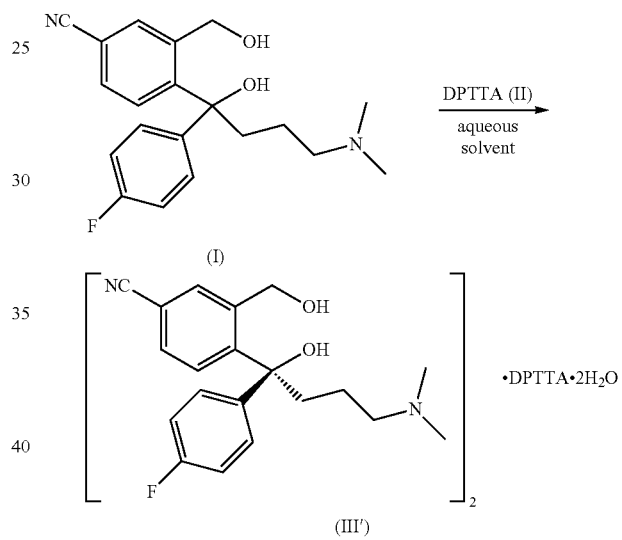

Racemic 5-cyano diol (34.2 g, 1.0 equivalent), D-(+)di-p-toluoyl tartaric add (20.1 g, 0.52 equivalent) were added, an ether solvent (513 mL) and a certain amount of water were added, the temperature was increased to 5060° C., the reaction was carried out under stirring for 2 hours. The temperature was decreased slowly to 30° C., a large amount of solids were precipitated, stirred for 60 minutes with the temperature kept. Filtered, the filter cake was washed by 30 mL ether solvent once. The filter cake was vacuum dried at 50° C. to obtain the resolved intermediate (III').

The results with different volume ratios of ether solvent to water are shown in table 3:

TABLE 3

| Solvent(V/V) | Yield | Chiral purity |
|---|---|---|
| Tetrahydrofuran/Water (99.8:0.2) | 48.2% | 99.5% |
| Tetrahydrofuran/Water (99.5:0.5) | 47.5% | 99.7% |
| Tetrahydrofuran/Water (95.0:5.0) | 41.5% | 99.4% |

TABLE 3-continued

| Solvent(V/V) | Yield | Chiral purity |
|---|---|---|
| Tetrahydrofuran/Water (90.0:10.0) | 38.5% | 99.5% |
| Methyltetrahydrofuran/Water (99.0:1.0) | 46.3% | 99.3% |
| Cyclopentyl methyl ether/Water (99.0:1.0) | 46.0% | 99.1% |
| Isopropyl ether/Water (99.0:1.0) | 45.1% | 99.0% |
| Dioxane/Water (99.0:1.0) | 46.2% | 99.6% |
| Dioxane/Water (90:10) | 36.2% | 99.6% |
| Diethylene glycol dimethyl ether/Water (99.0:1.0) | 46.0% | 99.5% |
| Ethylene glycol monomethyl ether/Water (99.0:1.0) | 40.0% | 97.9% |
| Ethylene glycol dimethyl ether/Water (99.0:1.0) | 44.7% | 99.0% |
| Ethylene glycol dibutyl ether/Water (99.0:1.0) | 46.5% | 99.3% |
| Propylene glycol dimethyl ether/Water (99.0:1.0) | 45.0% | 99.5% |
| Propylene glycol diethyl ether/Water (99.0:1.0) | 46.1% | 99.4% |

Comparative Example 1 (US2009/0069582 Example 1)

D-(+)di-p-toluoyl tartaric acid (15.0 g) was added, then n-propyl alcohol (118 mL) was added, the temperature was increased to 40° C., stirred for a complete dissolution, acetic acid (1.2 g) was added. Within 1 hour, the above solution of the resolving agent was added to the solution of racemic 5-cyano diol base (34.2 g) and n-propyl alcohol (32 mL), the temperature was kept at 40° C., the reaction was carried out under stirring for 2 hours. The temperature was decreased to 20~25° C., stirred crystallized for 2 hours with the temperature kept. Filtered, the filter cake was washed with n-propyl alcohol twice, crude resolved intermediate was obtained, chiral purity: S-5-cyano diol 91%-98%.

The crude product was added to a flask, n-propyl alcohol (86 mL) was added, the temperature was increased to 50° C., stirred for 2 hours, then cooled to 20~25° C., stirred and crystallized for 2 hours with the temperature kept. Filtered, the filter cake was washed with n-propyl alcohol, the filter cake was vacuum dried at 50° C., 18.5 g resolved intermediate was obtained, yield: 34.5%. The chiral purity of the resolved intermediate was: S-5-cyano did 99.3%.

Comparative Example 2 (WO2007/012954 Example 5)

Isopropanol (1125 ml) was added to racemic S-5-cyano diol (178.1 g), the temperature was increased to 50~55° C., stirred for a complete dissolution. D-(+)di-p-toluoyl tartaric acid (105 g) was added when the temperature was kept at 50~55° C., the temperature was decreased slowly to 25~30° C., stirred for 10 hours with the temperature kept. Filtered, the filter cake was washed with isopropanol twice, 110 ml for each time. The filter cake was vacuum dried at 50° C., 185 g crude resolved intermediate was obtained, chiral purity was: S-5-cyano diol 96:1%.

The crude product was added to a flask, isopropanol (1500 mL) was added, the temperature was increased to 80° C., stirred for a complete dissolution, then cooled to 20~25° C., stirred and crystallized for 1 hours with the temperature kept. Filtered, the filter cake was washed with isopropanol twice, 50 ml for each time, the filter cake was vacuum dried at 50° C., 101.2 g resolved intermediate was obtained, yield: 36.3%, the chiral purity was: S-5-cyano diol 99.1%.

The invention claimed is:

1. A method for resolution of 4-[4-dimethylamino-1-(4-fluorophenyl)-1-hydroxybutyl]-3-hydroxymethyl benzonitrile of formula I as an enantiomer thereof, comprising (a) mixing a compound of formula I and a resolving agent D-(+)di-p-toluoyl tartaric acid of formula II in a resolving solvent, (b) crystallizing a salt formed from (S)-4-[4-dimethylamino-1-(4-fluorophenyl)-1-hydroxy butyl]-3-hydroxymethyl benzonitrile of formula I' and said resolving agent in said resolving solvent, wherein said resolving solvent is an ether solvent:

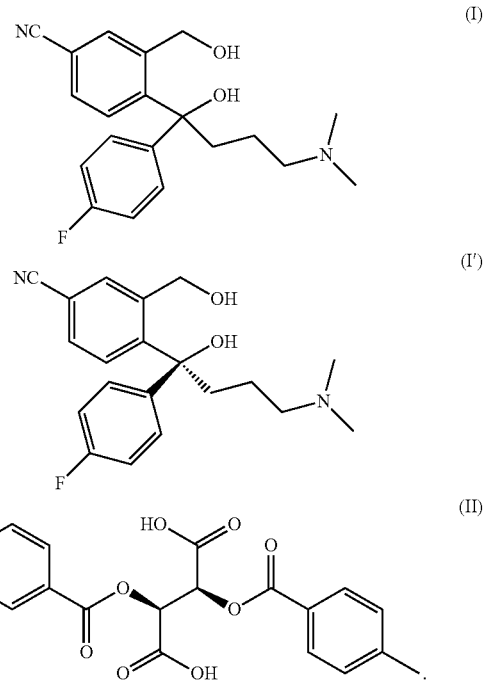

2. The method according to claim 1, characterized in that the volume percentage of water in the ether solvent is 0.2%-10%.

3. The method according to claim 1, characterized in that the volume percentage of water in the ether solvent is 0.2%-5%.

4. The method according to claim 1, wherein the ether solvent is selected from the group consisting of: tetrahydrofuran, methyltetrahydrofuran, cyclopentyl methyl ether, isopropyl ether, dioxane, ethylene glycol monomethyl ether, ethylene glycol dimethyl ether, ethylene glycol diethyl ether, ethylene glycol dibutyl ether, diethylene glycol dimethyl ether, propylene glycol dimethyl ether and propylene glycol diethyl ether.

5. The method according to claim 2, wherein the volume percentage of water in the ether solvent is 0.2%, 0.5%, 1.0%, 5.0% or 10.0%.

* * * * *

UNITED STATES PATENT AND TRADEMARK OFFICE
CERTIFICATE OF CORRECTION

PATENT NO. : 10,287,240 B2  
APPLICATION NO. : 15/521776  
DATED : May 14, 2019  
INVENTOR(S) : Zunjun Liang et al.

Page 1 of 1

It is certified that error appears in the above-identified patent and that said Letters Patent is hereby corrected as shown below:

On the Title Page

Item (73) Assignee, please change:  
Zhejiang Hushai Pharmaceuticals Co., Ltd., Zhejiang (CN)  
To:  
Zhejiang Huahai Pharmaceuticals Co., Ltd., Zhejiang (CN)

Signed and Sealed this  
Third Day of November, 2020

Andrei Iancu  
*Director of the United States Patent and Trademark Office*